United States Patent [19]

Bessin et al.

[11] Patent Number: 4,617,315

[45] Date of Patent: Oct. 14, 1986

[54] PHARMACEUTICAL COMPOSITIONS HAVING IMMUNO-SUPPRESSIVE PROPERTIES

[75] Inventors: Pierre Bessin, Chilly Mazarin; Jacqueline Bonnet, Paris, both of France

[73] Assignee: Albert Rolland, S.A., Paris, France

[21] Appl. No.: 738,043

[22] Filed: May 24, 1985

[51] Int. Cl.$^4$ .............................................. A61K 31/40
[52] U.S. Cl. .................................... 514/427; 514/429
[58] Field of Search ................................ 514/427, 429

[56] References Cited

U.S. PATENT DOCUMENTS 3,865,840 2/1975 Carson ................................ 548/531

OTHER PUBLICATIONS

Chem. Abst. 91-39315k (1979).
Chem. Abst. 92-58605s (1980).

Primary Examiner—Stanley J. Friedman
Attorney, Agent, or Firm—Omri M. Behr

[57] ABSTRACT

This invention relates to novel pharmaceutical compositions having immuno-suppressive activities, the active ingredient of which is a 4-aroyl N-alkyl or aryl pyrrolyl-2 carboxylic acid or a salt thereof.

The pharmaceutical compositions have therapeutic utility for treating auto-immune diseases, or in the prevention of rejection of graft organs.

3 Claims, No Drawings

PHARMACEUTICAL COMPOSITIONS HAVING IMMUNO-SUPPRESSIVE PROPERTIES

Novel pharmaceutical compositions having immuno-suppressive activities and method for using the same.

This invention relats to a novel use of derivatives of N-alkyl or N-aryl pyrrolyl-2 carboxylic acids. More precisely it relates to a novel therapeutic use of aroylated derivatives of N-alkyl or N-aryl pyrrolyl-2 carboxylic acids.

Specifically the subject matter of this invention provides pharmaceutical compositions endowed with immuno suppressive properties containing as active ingredient at least one 4-aroyl pyrrolyl-2 carboxylic acid derivative of the formula I

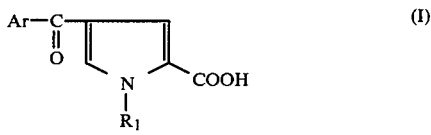

wherein Ar is a member selected from the group consisting of phenyl, halogenophenyl, naphtyl-1 and naphtyl-2 and $R_1$ is methyl or phenyl in conjunction or admixture with an inert non toxic pharmaceutically-compatible carrier or vehicle.

Similarly the active ingredient may also be an addition salt of a compound of formula I with a mineral or organic base-preferably a therapeutically-compatible base.

Some pyrrolyl-2 carboxylic acids are already known having been previously disclosed in the U.S. Pat. No. 2,479,972 as possessing local anaesthetizing properties. Other pyrrolyl alkanoic acids, namely 5-aroyl pyrrolyl alkanoic acids have already been disclosed in the U.S. Pat. No. 3,865,840. They found an utility as anti-inflammatory agents.

Moreover the derivatives of pyrrolyl carboxylic acids having the formula

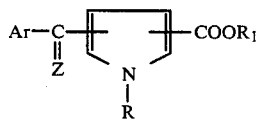

have been already disclosed in the French Pat. No. 2,405,246. They are endowad with uricosuric properties, or at least, they increase the rate of elimination of a colouring matter Phenol Red in the rats as did the known uricosuric agents.

The present invention substantially resides in the fact that some compounds disclosed in the French Pat. No. 3,405,246 and other related compounds which are not within the scope of the said French patent, evidence new properties of the immuno-depressive type.

The immuno-suppressive properties may be evidenced by the inhibition of the formation of rosettes shown after having contacted spleen cells of mice $C_{57}$ $BL_6$ with heterologous red blood cells of sheep. The inhibition is shown "in vitro" using concentrations of active compound of formula I ranging from 5 to 50 µg/ml.

As an example N-methyl 4-(naphtoyl-2) pyrrolyl-2 carboxylic acid is about as active as the known antimetabolic substance Azathioprine, taken as reference substance ($IC_{50}=6$ µg/ml).

In contrast to Azathioprine, the compounds of formula I are of reduced toxicity and particularly devoid of any toxicity on the blood cells.

The pharmaceutical compositions according to the invention are used for treating or alleviating the auto-immune diseases, such as erythematous lupus, rheumatoid polyarthritis, multiple sclerosis and also for preventing the refection of graft tissues.

Generally speaking these pharmaceutical compositions according to the invention, contain from 25 to 1000 mg of active ingredient per unit dosage and preferably from 50 to 500 mg per unit dosage.

The immuno-suppressive pharmaceutical compositions according to the invention are those intended for administration by oral, parenteral, rectal, permucous or percutaneous way of administration. For these purposes the pharmaceutical compositions will be in the form of uncoated or coated tablets, dragees, pills, capsules, soft gelatine capsules, drops, drinkable solutions or suspensions, suppositories, injectable solutions or suspensions or solutions in a polar medium for percutaneous applications.

The daily dosages may broadly vary depending of the nature of the auto-immune disease to be treated, on the age of the disease and the organic or articulary damages this disease has already caused. Preferably the daily dosage will range from 25 to 2000 mg of active ingredient in the man.

Among the compounds of formula I the most preferred ones are:
4-(2-bromobenzoyl) N-methylpyrrolyl-2 carboxylic acid
4-(naphtoyl-1) N-methyl pyrrolyl-2 carboxylic acid
4-(naphtoyl-2) N-methyl pyrrolyl-2 carboxylic acid.

In the foregoing, the base addition salts of the compounds of formula I are defined as the salts of an alkali metal base such as sodium, potassium, lithium, ammonium or rubidium; the salts of an earth-alkali metal base such as calcium or strontium; magnesium, aluminium or the ferrous metals. It may also be cited the alkylamine salts, the cyclo alkylamine salts, the aryl lower alkylamines salts, the pyridyl loweralkylamines salts, the furyl lower alkylamines salts, the hydroxy lower alkylamines salts, the aminoacids salts, the desoxyhexose or pentosamines salts, the aminohexitols or pentitols salts, the substituted guanidine salts, the polypeptides salts, and similar basic compounds.

The compounds of formula I are produced according to the process disclosed in the French Pat. No. 2,405,246 or by a chemically-obvious process.

The following examples are merely intended to illustrate the invention without limiting it in any manner.

EXAMPLE I

Tablets having 250 mg of 4-(Naphtoyl-2) N-methyl pyrrolyl-2 carboxylic acid

| | |
|---|---|
| 4-(Naphtoyl-2) N—methyl pyrrolyl-2 carboxylic acid | 250 g |
| Wheat starch | 180 g |
| Maize starch | 20 g |
| Colloidal silica | 10 g |
| Polymer of ethylene glycol and propylene glycol sold under the trade mark Pluronic F 68 | 25 g |
| Magnesium stearate | 40 g |
| Ethyl cellulose | 20 g |
| Talc | 15 g |

EXAMPLE II

Tablets having 300 mg of 4-(Naphtoyl-1) N-methyl pyrrolyl-2 carboxyli acid

| | |
|---|---|
| 4-(Naphtoyl-1) N—methyl pyrrolyl-2 carboxylic acid | 300 g |
| Magnesium phosphate | 150 g |
| Calcium sulphate | 60 g |
| Arabic gum | 15 g |
| Talc | 35 g |
| For 1000 tablets having a mean weight of .55 g. | |

EXAMPLE III

Soft gelatine capsules having 250 mg of 4-(2-bromobenzoyl) N-methyl pyrrolyl-2 carboxylic acid per unit dosage

| | |
|---|---|
| 4-(2-bromobenzoyl) N—methyl pyrrolyl-2 carboxylic acid | 250 g |
| Lactose | 125 g |
| Mannitol | 10 g |
| Talc | 12 g |
| Magnesium stearate | 13 g |
| For 1000 soft gelatine capsules having a mean weight of | 290 g |

EXAMPLE IV

Pharmacological studies on the immuno-suppressive properties of the compounds of formula I The immuno-suppressive properties have been evidenced on pharmacological tests, namely on models of auto-immune diseases in the rats:

polyarthritis after Freund's adjuvant in a curative or preventive therapy.

Allergic encephalitis in the Lewis rats.

The pharmaceutical compositions according to the invention have good effectivity in the polyarthritis after Freund's adjuvant from a daily dosage corresponding to 200 mg/kg per oral way, when administered to the steady state of the disease (from the 21st to the 35th day after injection of the Freund's adjuvant) i.e. in curative therapy-Using the same experimental conditions Azathioprine is inactive.

When the daily therapy is initiated as a preventive drug from the last day before the injection of Freund's adjuvant, the pharmaceutical compositions according to the invention are effective from a dosis corresponding to 100 mg/kg of active ingredient daily by oral way. In similar experimental conditions Azathioprine is effective from a dosage of 20 mg/kg.

Furthermore the pharmaceutical compositions according to the invention protect the rats against allergic encephalomyelitis:

at a dose of 100 mg/kg of active ingredient for two days: 50% protection at a dose of 400 mg/kg of active ingredient: 90% protection at a dose of 100 mg/kg Azathioprine affords a protection of 90%.

The pharmaceutical compositions according to the invention when administered at a dose of 400 mg/kg daily for 30 days do not alter the white blood cells and the red blood cells counts whilst Azathiprine from a dose of 20 mg/kg for the same set of time, causes a market decrease of the blood cells.

What we claim is:

1. A method of producing immuno-suppressive action which comprises administering to a subject in need of same a safe and effective amount of the active ingredient of least one compound of formula I

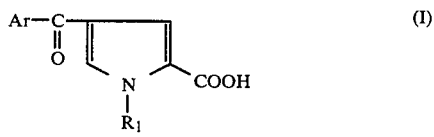

wherein Ar is a member selected from the group consisting of phenyl, halogenophenyl, naphthyl-1 and naphthyl-2 and $R_1$ is methyl or phenyl or the pharmaceutically acceptable mineral or organic base addition salts thereof.

2. A method for treating auto-immune diseases in humans which consists of administering daily to said patients suffering from an auto-immune disease a safe but effective amount of a compound of formula I or of claim 1 a base addition salt thereof.

3. A method according to claim 2 wherein the safe but effective amount of a compound of formula I ranges from 0.41 mg/kg to 33 mg/kg per day in the man.